(12) United States Patent
Allegrini et al.

(10) Patent No.: US 7,790,891 B2
(45) Date of Patent: Sep. 7, 2010

(54) PROCESS FOR THE PREPARATION OF PYRIDINE-METHYLSULFINYL COMPOUNDS

(75) Inventors: Pietro Allegrini, San Donato Milanese (IT); Marcello Rasparini, Pavia (IT); Gabriele Razzetti, Sesto San Giovanni (IT); Simone Mantegazza, Milan (IT); Vittorio Lucchini, San Donato Milanese (IT); Alberto Bologna, Vidigulfo (IT)

(73) Assignee: Dipharma Francis S.R.L., Baranzate (IT)

( * ) Notice: Subject to any disclaimer, the term of this patent is extended or adjusted under 35 U.S.C. 154(b) by 67 days.

(21) Appl. No.: 11/927,009

(22) Filed: Oct. 29, 2007

(65) Prior Publication Data

US 2009/0076277 A1    Mar. 19, 2009

(30) Foreign Application Priority Data

Oct. 30, 2006 (IT) .......................... MI2006A2086
Jun. 15, 2007 (IT) .......................... MI2007A1208

(51) Int. Cl.
*C07D 471/02* (2006.01)
*C07D 401/12* (2006.01)

(52) U.S. Cl. .................................. 546/118; 546/273.7
(58) Field of Classification Search .............. 546/273.7, 546/118
See application file for complete search history.

(56) References Cited

FOREIGN PATENT DOCUMENTS

| EP | 0484265 A | 5/1992 |
|---|---|---|
| EP | 2063705 A1 | 1/1995 |
| EP | 1 674 463 A1 | 6/2006 |
| ES | 2 063 705 A1 | 1/1995 |
| WO | 9840377 A | 9/1998 |
| WO | 9840378 A | 9/1998 |

OTHER PUBLICATIONS

Partial European Search Report issued in the corresponding European Application No. EP 07117670.5 completed on Feb. 26, 2008 and mailed on Mar. 5, 2008.

European Search Report issued in the corresponding European Application No. EP 07 11 7670, completed on Jun. 9, 2008 and mailed on Jun. 9, 2008.

*Primary Examiner*—Patricia L Morris
(74) *Attorney, Agent, or Firm*—Griffin & Szipl, P.C.

(57) ABSTRACT

A process for the preparation of a compound of formula (I), or a salt thereof,

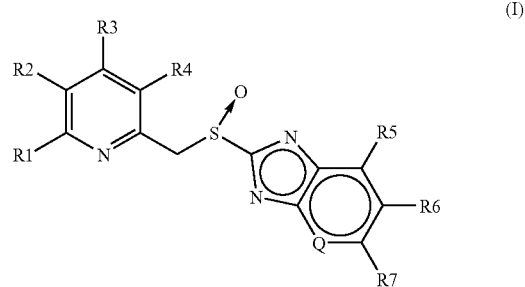

(I)

wherein Q is =CR$_8$— or =N—; and R$_1$-R$_8$ are as herein defined; comprising the reaction of a compound of formula (II), or a salt thereof,

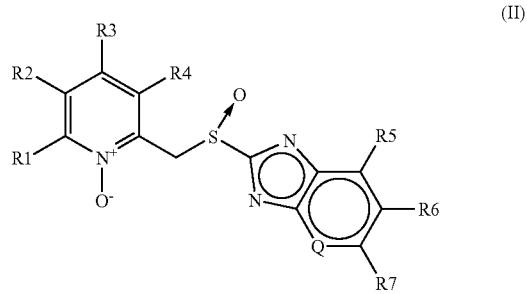

(II)

wherein Q, R$_1$-R$_7$ are as herein defined; with a reducing agent selected from a trivalent phosphorous compound, an oxidizable solvent and a sulfonic acid chloride; and, if desired, the conversion of a compound of formula (I) to another compound of formula (I) or a salt thereof.

7 Claims, 2 Drawing Sheets

PROCESS FOR THE PREPARATION OF PYRIDINE-METHYLSULFINYL COMPOUNDS

This application claims priority from Italian Patent Application No. MI2006A002086, filed Oct. 30, 2006 and from Italian Patent Application No. MI2007A1208 filed Jun. 15, 2007, the entire disclosure of which is incorporated herein by reference.

FIELD OF THE INVENTION

The present invention relates to a novel process for the preparation of pyridine-methylsulfinyl compounds useful in therapy.

TECHNOLOGICAL BACKGROUND

Pyridine-methylsulfinyl compounds act as proton pump inhibitors and are used in the treatment of pathologies related to an increase in gastric secretion. Examples of these compounds, known as "prazoles", are omeprazole, esomeprazole, pantoprazole, rabeprazole, lansoprazole, tenatoprazole and hydroxymeprazole.

The synthesis of these products is substantially carried out following the scheme reported below, wherein $R_1$-$R_7$ and Q are for example as herein defined.

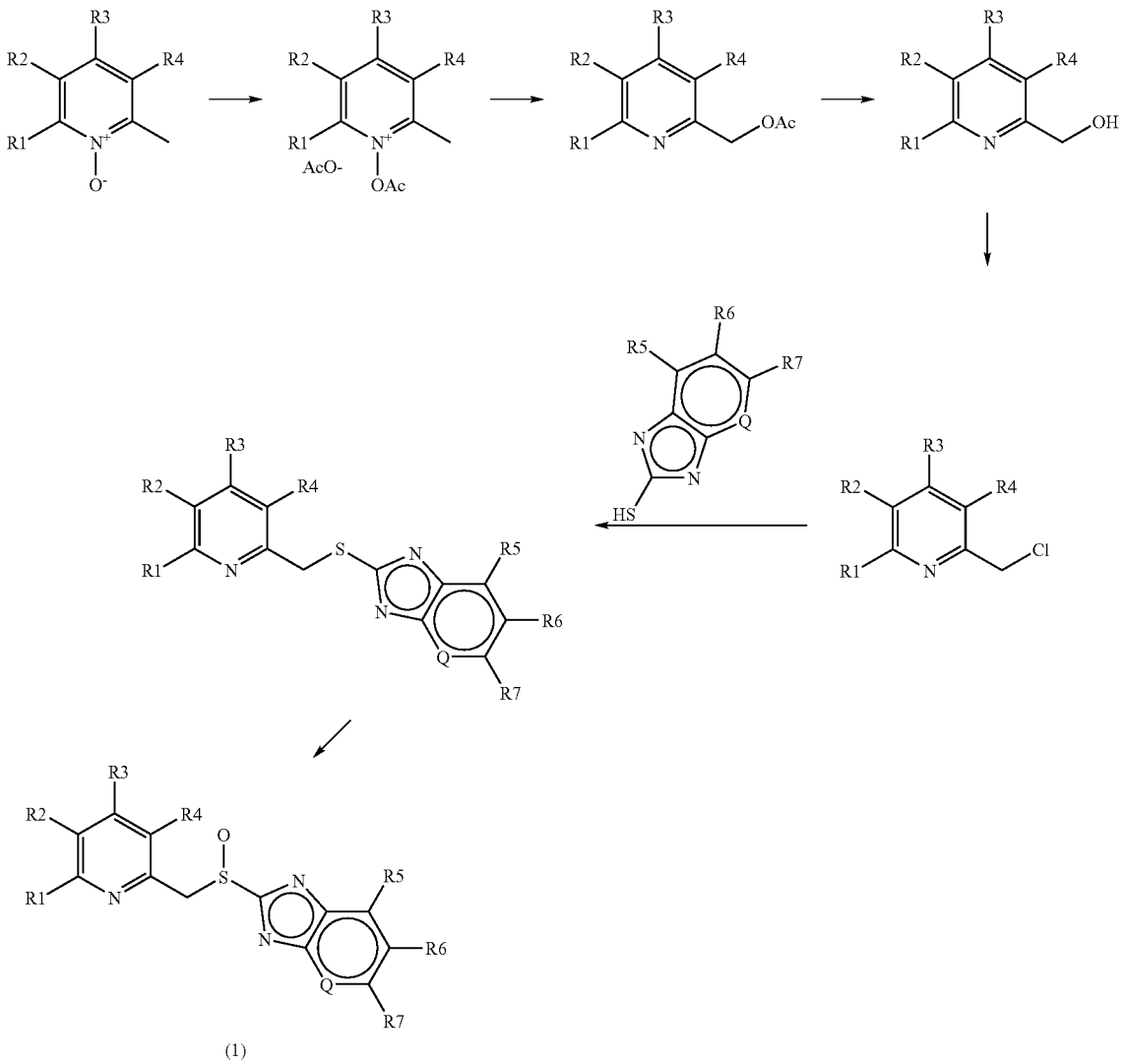

(1)

It is evident that such synthesis requires a number of complex steps.

WO 98/40378 discloses the synthesis of "prazoles" by reduction of the respective N-oxides. The exemplified reducing agents for carrying out this reaction are dangerous to handle (for example Ni-Raney), sometimes incompatible with the substrate to be reduced (for example Ni-Raney/$H_2$ or Ru/$H_2$), or difficulty available on the market (for example bis-thiomorpholine) and expensive. Furthermore, the synthesis of the intermediate N-oxide reported therein involves a complex, time-consuming process. This makes the process incompatible with the requirements for the industrial production and evidences the need for improved synthetic methods.

SUMMARY OF THE INVENTION

A novel process has now been found for the preparation of pyridine-methylsulfinyl compounds having the formula (I) herein reported, which overcomes the above mentioned technical problems and provides said compounds and the salts thereof in a purity degree purity equal to or higher than 99.5%.

BRIEF DISCLOSURE OF THE FIGURES

Figure 1:
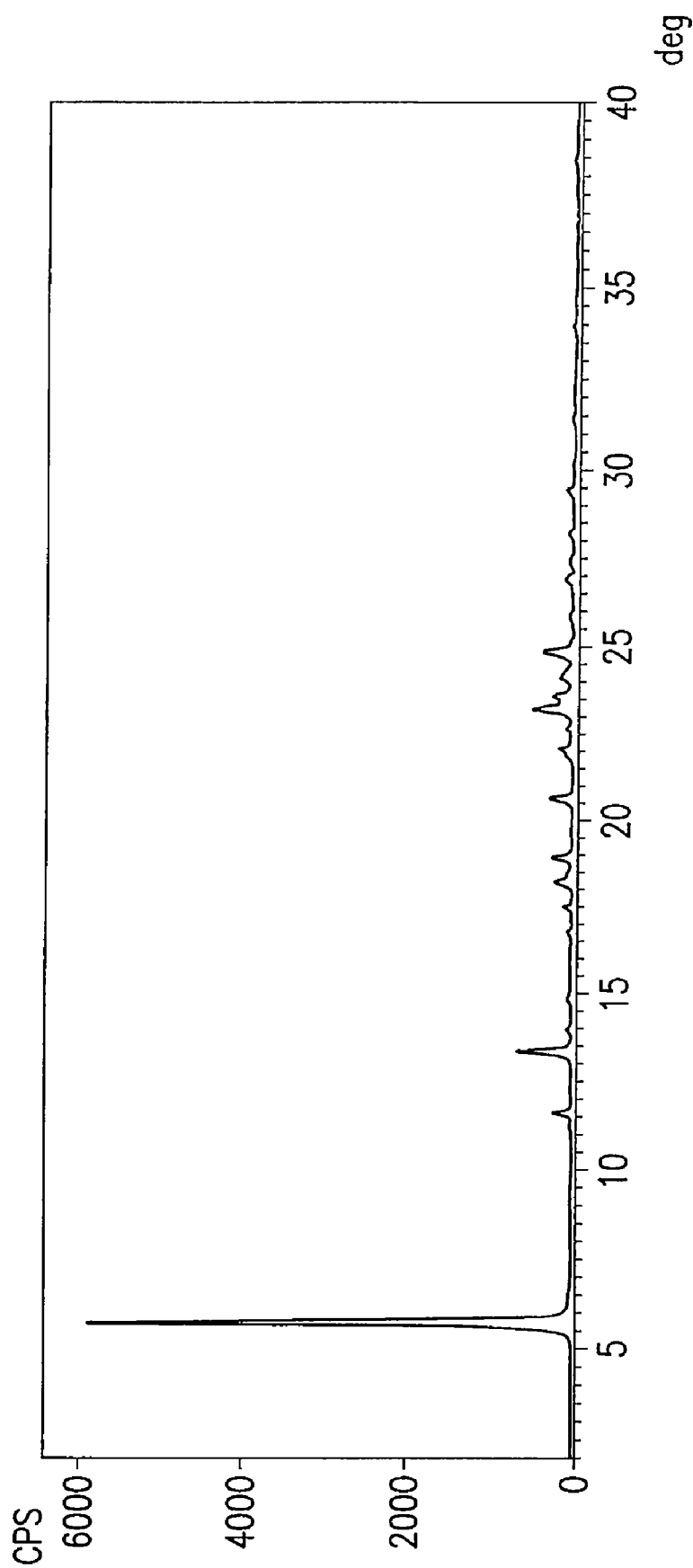
Figure 2:
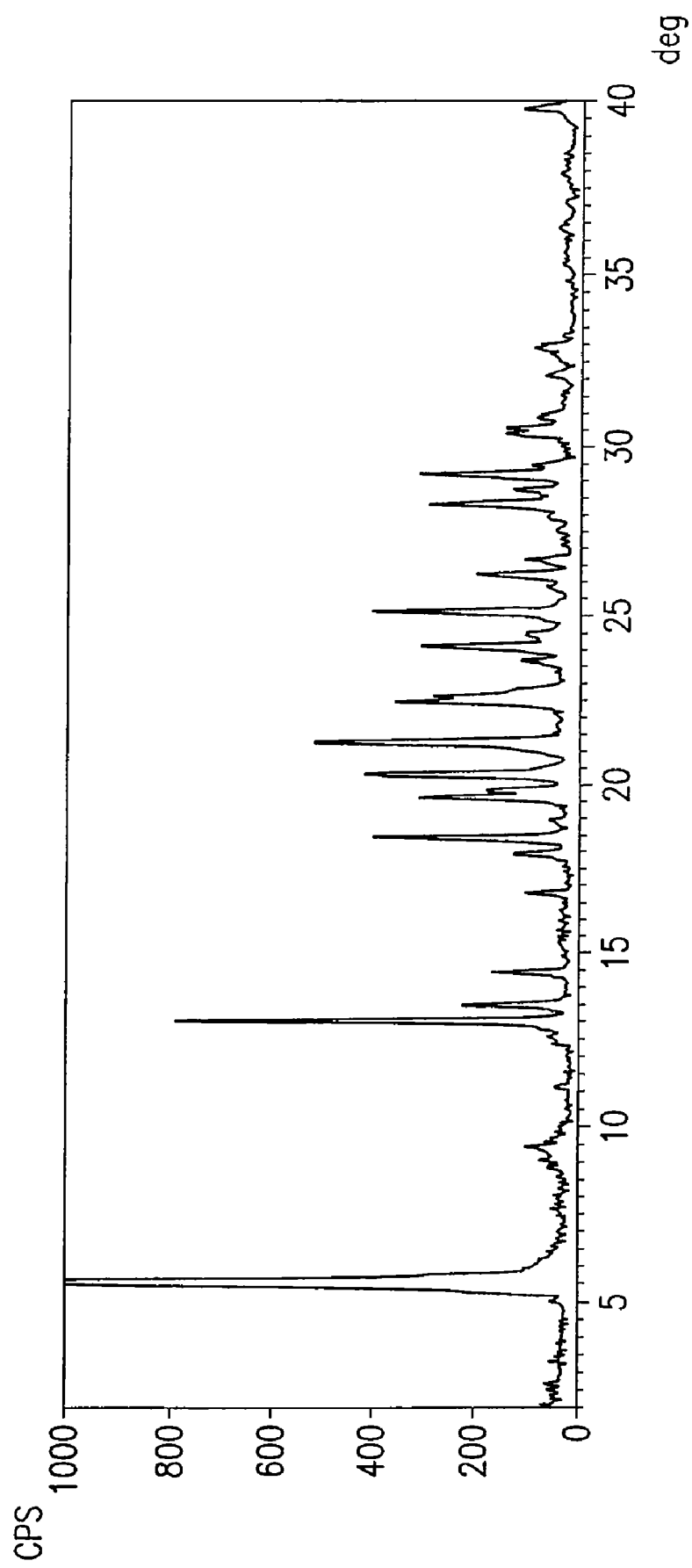

FIG. 1 and FIG. 2 report the X-ray diffraction spectra (XRPD) of two crystalline forms, respectively Form I and Form II, of the intermediate of formula (II), 2-[4-(3-methoxypropoxy)-3-methyl-1-oxypyridin-2-yl-methylsulfinyl]-1H-benzimidazole, recorded with the automatic diffractometer APD 2000 θ/θ (Ital-Structures) under the following operative conditions: CuKα radiation (λ=1.5418 Å), scanning with angular interval 3-40°, with angular step of 0.03° for 1 sec.

DETAILED DISCLOSURE OF THE INVENTION

The object of the invention is a process for the preparation of a compound of formula (I), or a salt thereof, either as a single isomer or as a mixture thereof,

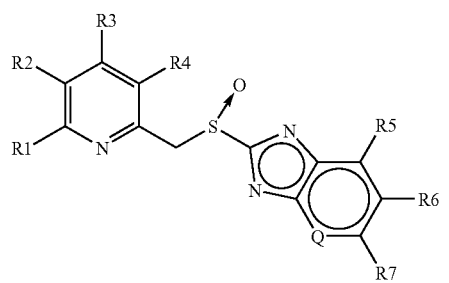

(I)

wherein

Q is =$CR_8$— or =N—;

each of $R_1$, $R_2$, $R_3$ and $R_4$ is independently selected from hydrogen, halogen, hydroxy, nitro, $C_1$-$C_6$ alkyl optionally substituted by hydroxy; $C_1$-$C_6$ alkylthio; $C_1$-$C_6$ alkoxy optionally substituted by halogen or $C_1$-$C_6$ alkoxy; phenyl-$C_1$-$C_6$ alkyl; phenyl-$C_1$-$C_6$ alkoxy; and —$N(R_aR_b)$ wherein each of $R_a$ and $R_b$ is independently hydrogen or $C_1$-$C_6$ alkyl or $R_a$ and $R_b$, taken together with the nitrogen atom they are linked to, form a saturated heterocyclic ring; and each of $R_5$, $R_6$, $R_7$ and $R_8$ is independently selected from hydrogen, halogen, hydroxy; $C_1$-$C_6$ alkyl optionally substituted by hydroxy; $C_1$-$C_6$ alkylthio; $C_1$-$C_6$ alkoxy optionally substituted by halogen; $C_1$-$C_6$ alkyl-carbonyl, $C_1$-$C_6$ alkoxy-carbonyl, and oxazol-2-yl;

comprising the reduction reaction of a compound of formula (II), or a salt thereof, both as the isomeric mixture and as an individual isomer,

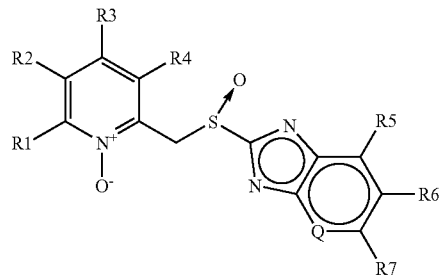

(II)

wherein Q and $R_1R_7$ are as defined above;
a) with a compound selected from a trivalent phosphorous compound and an oxidizable solvent; in the presence of a catalyst; and, if necessary, in the presence of a basic agent and, if the case, in a solvent; or
b) with a sulfonic acid chloride, in the presence of a basic agent; and, if necessary, in an organic aprotic solvent; and, if desired, the conversion of a compound of formula (I) to another compound of formula (I), and, if the case, the conversion of a compound of formula (I) to a salt thereof or vice versa.

An isomer of a compound of formula (I) or (II) can be for example a geometrical or optical isomer thereof, preferably an (R) or (S) enantiomer.

Each of $R_1$-$R_8$, independently, as halogen atom can be for example fluorine, chlorine or bromine.

An alkyl group or residue in one of the $R_1$-$R_8$ substituents is preferably a straight or branched $C_1$-$C_4$ alkyl group, in particular methyl, ethyl, propyl, isopropyl, butyl or tert-butyl, more preferably methyl, ethyl or propyl.

A hydroxy-substituted $C_1$-$C_6$ alkyl group is preferably a $C_1$-$C_4$ alkyl group substituted with one or two hydroxy groups, in particular —$CH_2OH$.

A halo-substituted $C_1$-$C_6$ alkoxy group is preferably a $C_1$-$C_4$ alkoxy group substituted with one, two or three halogen atoms as defined above, more preferably two or three fluorine atoms, in particular —$OCHF_2$ or —$OCH_2CF_3$.

A $C_1$-$C_6$ alkoxy-substituted $C_1$-$C_6$ alkoxy group is typically a $C_1$-$C_4$ alkoxy-substituted $C_1$-$C_4$ alkoxy group, preferably $C_1$-$C_3$ alkoxy-$OCH_3$, in particular —OR—$(CH_2)_3$—$OCH_3$.

A —$N(R_aR_b)$ group is preferably an amino, methylamino, ethylamino, propylamino, dimethylamino group. When $R_a$ and $R_b$, taken together with the nitrogen atom they are linked to, form a saturated heterocyclic ring, this can be a 5- or 6-membered heterocycle optionally containing a further nitrogen or oxygen atom. Examples of said group are pyrrolidino, piperidino, piperazino and morpholino.

Preferred compounds of formula (I) are those in which:
Q is =CH— or =N—;
$R_2$ is hydrogen, or $C_1$-$C_4$ alkyl optionally substituted by hydroxy;
$R_3$ is $C_1$-$C_4$ alkoxy optionally substituted by $C_1$-$C_4$ alkoxy or halogen;
$R_4$ is $C_1$-$C_4$ alkyl or $C_1$-$C_4$ alkoxy;
$R_6$ is hydrogen or $C_1$-$C_4$ alkoxy optionally substituted by halogen;
$R_7$ is hydrogen or $C_1$-$C_4$ alkoxy; and
$R_1$ and $R_5$ are hydrogen.

Specific examples of compounds of formula (I) are:
2-(3,4-dimethoxypyrid-2-yl)methanesulfinyl-5-difluoromethoxy-1H-benzimidazole (pantoprazole);

2-(4-chloro-3-methoxypyrid-2-yl)methanesulfinyl-5-difluoromethoxy-1H-benzimidazole;

5-methoxy-2-{[(4-methoxy-3,5-dimethyl-2-pyridinyl)methyl]sulfinyl}-1H-benzimidazole (omeprazole);

5-methoxy-2-{[(4-methoxy-3-methyl-5-hydroxymethyl-2-pyridinyl)-methyl]sulfinyl}-1H-benzimidazole (hydroxymeprazole);

2-{[3-methyl-4-(2,2,2-trifluoroethoxy)-2-pyridinyl)methyl]sulfinyl}-1H-benzimidazole (lansoprazole);

2-{[3-methyl-4-(3-methoxy-propoxy)-2-pyridinyl)methyl]sulfinyl}-1H-benzimidazole (rabeprazole); and 5-methoxy-2-{[(4-methoxy-3,5-dimethyl-2-pyridinyl)methyl]sulfinyl}-1H-imidazo[4,5-b]pyridine (tenatoprazole); and the salts thereof.

A trivalent phosphorous compound as reducing agent can be for example a P(III) halide, such as $PCl_3$ or $PBr_3$, preferably phosphorous trichloride; a phosphorous acid alkyl or aryl ester, e.g. a tri-($C_1$-$C_4$ alkyl) phosphite or triphenyl phosphite $P(OR—C_6H_5)_3$, preferably triethyl phosphite $P(OR—C_2H_5)_3$; an organic phosphine, typically a tri-($C_1$-$C_4$ alkyl) phosphine having the alkyl group optionally substituted with hydroxy, such as tri-butyl phosphine and tri(3-hydroxypropyl) phosphine; a tri-($C_5$-$C_7$ cycloalkyl) phosphine, e.g. tri(cyclohexyl) phosphine; a triaryl or tri-heteroaryl phosphine, e.g. triphenyl phosphine, tri(o-tolyl) phosphine, trifuryl phosphine. Preferably triphenyl phosphine or triethyl phosphite.

An oxidizable solvent is for example an alcoholic solvent, typically a straight or branched $C_1$-$C_4$ alkanol, having 1 to 3 hydroxy groups, such as methanol, ethanol, 2-propanol, 1- or 2-butanol or glycerin; preferably methanol, ethanol or 2-propanol, in particular methanol.

When the reducing agent is a trivalent phosphorous derivative, the catalyst can be for example a transition metal salt or complex, typically Mo, Ru, V, Mn, Fe, W and Re; preferably sodium metavanadate [$NaVO_3$], vanadyl acetylacetonate [$VO(acac)_2$], vanadous chloride [$VCl_2$], (tetraphenylporphyrinate)Mn(III)Cl, (tetraphenylporphyrinate)-Fe(III)Cl, (tetraphenylporphyrinate)Fe(II), sodium or ammonium molybdate [$(NH)_2MoO_4$] or [$Na_2MoO_4$], salts and complexes containing the species $MoO_2$, such as dichlorodioxomolybdenum [$Cl_2MoO_2$] optionally as complex with dimethylformamide (DMF), or dioxomolybdenum bis dialkyldithiocarbamates, such as $(Et_2NCS_2)_2MoO_2$, ruthenium(III) salts, such as $RUCl_3$, or the hydrated forms or complexes thereof, such as K[(H-Edta)RuCl], tungsten (VI) oxychloride [$WOCl_4$], methyl trioxorhenium(VII) [$CH_3ReO_3$]. More preferably $RuCl_3$ or its hydrated forms, methyl trioxorhenium (VII) [$CH_3ReO_3$], and dichlorodioxomolybdenum [$Cl_2MoO_2$] optionally as a complex with dimethylformamide; in particular dichlorodioxomolybdenum as a complex with dimethylformamide.

When the reducing agent is an oxidizable solvent, as defined above, one of the catalysts reported above can be used; in particular when the alkanol is methanol, ethanol or 2-propanol, then the catalyst is preferably $RuCl_3$ or a hydrated form thereof, known in the art.

A sulfonic acid chloride is for example a $C_1$-$C_6$ alkylsulfonyl chloride, an optionally substituted aryl-$C_1$-$C_6$ alkylsulfonyl chloride; or an optionally substituted arylsulfonyl chloride.

A $C_1$-$C_6$ alkylsulfonyl chloride, which can be straight or branched, is preferably an optionally substituted $C_1$-$C_4$ alkylsulfonyl chloride, more preferably methylsulfonyl chloride, ethylsulfonyl chloride, butylsulfonyl chloride, in particular methylsulfonyl chloride.

An aryl-$C_1$-$C_6$ alkylsulfonyl chloride is for example a phenyl-$C_1$-$C_6$ alkylsulfonyl chloride or a naphthyl-$C_1$-$C_6$ alkylsulfonyl chloride, in particular a phenyl-$C_1$-$C_4$ alkylsulfonyl chloride. When substituted, said group can be substituted at the aryl and/or alkyl moiety with 1 to 5 substituents independently selected from halogen, for example chlorine, bromine or iodine, nitro and $C_1$-$C_4$ alkyl, for example methyl. A preferred example of aryl-$C_1$-$C_6$ alkylsulfonyl chloride is benzylsulfonyl chloride.

An arylsulfonyl chloride is for example phenylsulfonyl chloride or naphthylsulfonyl chloride, in particular phenylsulfonyl chloride. When substituted, this can be substituted with 1 to 5 substituents independently selected from halogen, for example chlorine, bromine or iodine, nitro, and $C_1$-$C_6$ alkyl, for example methyl. Preferred examples of arylsulfonyl chloride are benzenesulfonyl chloride, p-toluenesulfonyl chloride, p-nitrobenzenesulfonyl chloride, p-bromobenzenesulfonyl chloride.

A basic agent is for example an inorganic or organic base, typically an alkali or alkaline-earth metal, preferably lithium, sodium, potassium or calcium, carbonate or hydroxide; in particular sodium, potassium, lithium or calcium hydroxides; and sodium or potassium carbonates; or a tertiary organic amine such as triethylamine or ethyldiisopropylamine, or a secondary cyclic amine such as piperidine, piperazine or morpholine, or a tertiary cyclic amine such as N-methyl piperidine or N-methyl morpholine, or a diamine, for example, tetramethylethylenediamine.

According to alternative a) of the process of the invention, a basic agent is preferably tetramethylethylenediamine or morpholine. According to alternative b) preferably the basic agent is triethylamine or ethyldiisopropylamine, more preferably ethyldiisopropylamine.

According to alternative a) of the process of the invention, a solvent can be water or an organic protic or aprotic solvent, or mixture of two to four, in particular 2 or 3, of said solvents.

An organic solvent is typically an ether, e.g. tetrahydrofuran, dioxane, diethyl ether; a $C_1$-$C_6$ alkanol e.g. methanol, ethanol or isopropanol; an aliphatic hydrocarbon, e.g. hexane, heptane or cyclohexane; an aromatic hydrocarbon, e.g. example toluene; an ester solvent, e.g. ethyl acetate or butyl acetate; or a dipolar aprotic solvent, e.g. acetonitrile, dimethylformamide, dimethylacetamide or dimethylsulfoxide. Preferably said solvent is a $C_1$-$C_4$ alkanol, particularly methanol or ethanol.

When the reducing agent is an oxidizable solvent as herein defined, preferably the solvent is the reducing agent itself.

According to alternative b) of the process of the invention, an organic aprotic solvent can be a single solvent or a mixture of two to four, in particular 2 or 3, of said solvents. An organic solvent is typically an ether, e.g. tetrahydrofuran, dioxane, diethyl ether; an aliphatic hydrocarbon, e.g. hexane, heptane or cyclohexane; an aromatic hydrocarbon, e.g. toluene; a chlorinated solvent, e.g. dichloromethane or dichloroethane; an ester solvent, e.g. ethyl acetate or butyl acetate; or a dipolar aprotic solvent, e.g. acetonitrile, dimethylformamide, dimethylacetamide or dimethylsulfoxide. Preferably said solvent is dichloromethane or acetonitrile, more preferably acetonitrile.

According to alternative a) of the process, the reduction reaction of a compound (II), or a salt thereof, can be carried out at a temperature approximately ranging from −10° C. to the reflux temperature of the solvent or reaction mixture.

When the reducing agent is a trivalent phosphorous derivative, the stoichiometric ratio of said reducing agent to a compound (II) or a salt thereof can approximately range from 1.0 to 3.0; preferably approximately from 1.0 to 1.2.

The catalyst can be present in a molar amount ranging from 0.5 to 20%, preferably from 1 to 10%, with respect to the amount of compound (II).

The stoichiometric ratio of basic agent equivalents to mols of compound (II), or a salt thereof, can approximately range from 1.0 to 30.0; preferably approximately from 9.0 to 15.0, more preferably about 12.

According to alternative b) of the process, the reaction can be carried out at a temperature approximately ranging from −20° C. to the reflux temperature of the solvent or reaction mixture, preferably from −15° C. to 0° C.

The stoichiometric ratio of a sulfonic acid chloride to a compound (II) or a salt thereof can approximately range from 1.0 to 6.0; preferably approximately from 3.0 to 4.0.

The stoichiometric ratio of basic agent equivalents to mols of a compound (II) or a salt thereof can approximately range from 1.0 to 20.0; preferably approximately from 8.0 to 16.0; more preferably approximately from 11.8 to 12.2.

The conversion of a compound of formula (I) to another compound of formula (I), or a salt thereof, and vice versa, can be carried out with known methods.

A thus obtained compound of formula (I), for example 2-{[3-methyl-4-(3-methoxypropoxy)-2-pyridinyl)methyl]sulfinyl}-1H-benzimidazole, or a salt thereof, has purity degree equal to or higher than 99.5%, in particular of about 99.9% or higher.

The invention also provides a novel process for the preparation of a compound of formula (II), or a salt thereof, either as single, in particular as geometrical or optical, isomer or as a mixture thereof

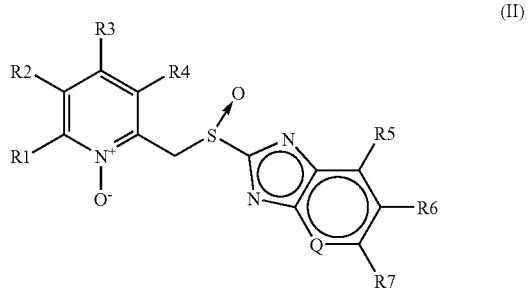
(II)

wherein Q and $R_1$-$R_7$ are as defined above;

comprising the reaction of a compound of formula (III), or a salt thereof

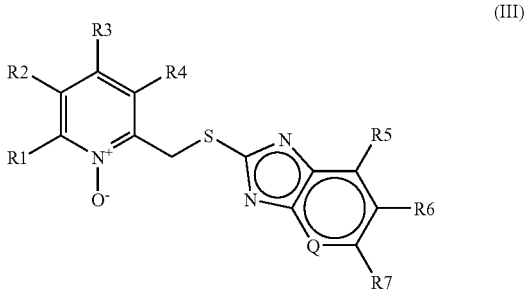
(III)

wherein Q and $R_1$-$R_7$ are as defined above, with an oxidizing agent, if necessary, in the presence of a catalyst, if necessary, by heating, if necessary, in the presence of a basic agent and, if the case, in a solvent.

If desired, a compound of formula (II), or a salt thereof, can be converted to another compound of formula (II), or a salt thereof, according to known methods.

A salt of a compound of formula (I), (II) or (III) is preferably an acid or base addition salt, preferably a pharmaceutically acceptable salt, for example the sodium salt.

An oxidizing agent can be an organic peracid, for example meta-chloroperbenzoic acid, peracetic acid, trifluoroperacetic acid, monoperoxyphthalic acid or salts thereof, or phthalimidoperoxyhexanoic acid; or a peroxide, e.g. hydrogen peroxide, or its addition compounds such as urea-hydrogen peroxide, or sodium percarbonate, tert-butylhydroperoxide, cyclohexyl hydroperoxide, 2-hydroperoxyhexafluoro-2-propanol; or a dioxirane such as dimethyldioxirane or methyl (trifluoromethyl)dioxirane; or a hypochlorite such as sodium hypochlorite or tert-butyl hypochlorite; or N-chlorosuccinimide or N-bromosuccinimide or chloramine-T, or with sodium periodate or potassium peroxodisulfate ($K_2S_2O_8$) or potassium hydrogen persulfate ($KHSO_5$). Preferably, the oxidizing agent is sodium hypochlorite.

A catalyst can be a transition metal salt or complex of a metal chosen from Mo, V and W, as the sodium molybdate [$Na_2MoO_4$], ammonium molybdate [$(NH_4)_2MoO_4$], sodium metavanadate [$NaVO_3$], vanadyl acetyl acetonate [$VO(Acac)_2$] or sodium tungstate [$Na_2WO_4$].

A basic agent can be for example an alkali or alkaline-earth metal hydroxide or carbonate, preferably lithium, sodium, potassium or calcium; preferably sodium, potassium, lithium or calcium hydroxides, sodium or potassium carbonates; in particular sodium hydroxide.

A solvent can be water or an organic protic or aprotic solvent, as defined above, or a mixture of two to four, in particular 2 or 3, of said solvents; in particular a mixture of acetonitrile and water.

The oxidation reaction of a compound (III), or a salt thereof, either with or without a catalyst, can be carried out at a temperature approximately ranging from −10° C. to the reflux temperature of the solvent or reaction mixture; preferably, at a temperature approximately ranging from 0° C. to 30° C.

The stoichiometric ratio of a compound (III), or a salt thereof, to an oxidizing agent can approximately range from 0.8 to 1.2, preferably approximately from 0.9 to 0.95.

The catalyst can be present in molar amounts ranging from 0.5 to 20%, preferably from 1 to 10%, with respect to the amount of compound (III), or a salt thereof.

A thus obtained compound of formula (II), or a salt thereof, can further be reacted with a reducing agent, for example according to the alternative processes a) and b) described above, to obtain a compound of formula (I), or a salt thereof, as herein defined.

A thus obtained compound of formula (II), for example 2-[4-(3-methoxypropoxy)-3-methyl-1-oxypyridin-2-yl-methylsulfinyl]-1H-benzimidazole, or a salt thereof, in particular in the crystalline form, has purity degree equal to or higher than 99.5%, in particular about 99.9% or higher.

The compound 2-[4-(3-methoxypropoxy)-3-methyl-1-oxypyridin-2-yl-methylsulfinyl]-1H-benzimidazole, in particular in the crystalline form, and the salts thereof, are novel compounds and a further object of the invention. Said compound is herein obtained in two crystalline forms, respectively Form I and Form II. Form I has the XRPD spectrum as reported in FIG. 1 wherein the most intense diffraction peaks fall at 5.7; 11.6; 13.3; 18.2; 18.9; 20.6; 23.2; 23.6; 24.1; 24.8; ±0.2° in 2θ. Form II has the spectrum XRPD as reported in FIG. 2 wherein the most intense diffraction peaks fall at 5.5; 13.0; 18.4; 19.6; 20.3; 21.2; 22.4; 24.0; 25.1; 28.3 and 29.1±0.2° in 2θ.

A compound of formula (III) can be prepared according to known methods, for example by reaction of a compound of formula (IV), or a salt thereof,

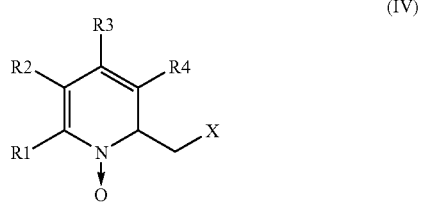

wherein X is a leaving group, for example chlorine, and $R_1$, $R_2$, $R_3$ and $R_4$ are as herein defined; with a compound of formula (V) or a salt thereof

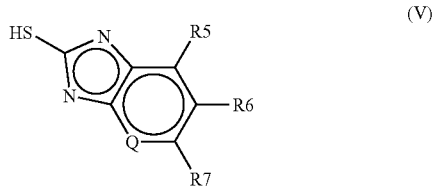

wherein Q, $R_5$, $R_6$ and $R_7$ are as herein defined; in the presence of a base, at room temperature, and the optional conversion of the resulting compound to another compound of formula (III).

The following examples illustrate the invention:

EXAMPLE 1

2-{[3-Methyl-4-(3-methoxypropoxy)-2-pyridinyl) methyl]sulfinyl}-1H-benzimidazole (I)

Rabeprazole Sodium Salt

A 3-necked round-bottom flask equipped with reflux condenser, thermometer and magnetic stirring, under nitrogen atmosphere, is loaded with 2-[4-(3-methoxypropoxy)-3-methyl-1-oxypyridin-2-yl-methylsulfinyl]-1H-benzimidazole sodium salt (intermediate II) (1.0 g; 2.5 mmols), absolute ethanol (20 ml), morpholine (100 mg; 1.1 mmols) and $RuCl_3$ hydrate (40% w/w Ru; 25 mg; 0.1 mmols). The reaction mixture is heated to 50° C. for 8 hours, then cooled to room temperature and filtered through Celite®. Upon concentration the title product is obtained. Yield: approximately 70%.

$^1$H NMR (DMSO-$d_6$): 1.98 (2H, m); 2.16 (3H, s); 3.52 (3H, s); 3.49 (2H, t); 4.10 (2H, t); 4.47 & 4.71 (2H, dd); 6.93 (3H, m); 7.49 (2H, m); 8.28 (1H, d).

$^{13}$C NMR (DMSO-$d_6$): 10.78; 28.67; 57.95; 59.92; 64.98; 68.32; 106.00; 117.18; 118.74; 121.76; 145.80; 147.97; 152.13; 161.55; 162.66.

Following an analogous procedure, starting from the respective intermediate of formula (II) or its sodium salt, the following compounds or the sodium salts thereof are obtained:

2-(4-chloro-3-methoxypyrid-2-yl)methanesulfinyl-5-difluoromethoxy-1H-benzimidazole;
5-methoxy-2-{[(4-methoxy-3,5-dimethyl-2-pyridinyl)methyl]sulfinyl}-1H-benzimidazole;
5-methoxy-2-{[(4-methoxy-3-methyl-5-hydroxymethyl-2-pyridinyl)-methyl]sulfinyl}-1H-benzimidazole;
2-{[3-methyl-4-(2,2,2-trifluoroethoxy)-2-pyridinyl)methyl] sulfinyl}-1H-benzimidazole;
5-methoxy-2-{[(4-methoxy-3,5-dimethyl-2-pyridinyl)methyl]sulfinyl}-1H-imidazo[4,5-b]pyridine; and
2-(3,4-dimethoxypyrid-2-yl)methanesulfinyl-5-difluoromethoxy-1H-benzimidazole.

EXAMPLE 2

2-{[3-Methyl-4-(3-methoxypropoxy)-2-pyridinyl) methyl]sulfinyl}-1H-benzimidazole (I)

Rabeprazole Sodium Salt

A 3-necked round-bottom flask equipped with reflux condenser, thermometer and magnetic stirring, under nitrogen atmosphere, is loaded with 2-[4-(3-methoxypropoxy)-3-methyl-1-oxypyridin-2-yl-methylsulfinyl]-1H-benzimidazole sodium salt (intermediate II) (1.0 g; 2.5 mmols), absolute ethanol (20 ml), triethyl phosphite (460 mg; 2.75 mmols) and $Cl_2MoO_2*2$ DMF (43 mg; 0.12 mmols). The mixture is heated to 50° C. for 2 hours, cooled and filtered through Celite®. Upon concentration the title product is obtained.
Yield: approximately 40%.

Following an analogous procedure, the following compounds are obtained as sodium salts:
2-(4-chloro-3-methoxypyrid-2-yl)methanesulfinyl-5-difluoromethoxy-1H-benzimidazole;
5-methoxy-2-{[(4-methoxy-3,5-dimethyl-2-pyridinyl)methyl]sulfinyl}-1H-benzimidazole;
5-methoxy-2-{[(4-methoxy-3-methyl-5-hydroxymethyl-2-pyridinyl)-methyl]sulfinyl}-1H-benzimidazole;
2-{[3-methyl-4-(2,2,2-trifluoroethoxy)-2-pyridinyl)methyl] sulfinyl}-1H-benzimidazole;
5-methoxy-2-{[(4-methoxy-3,5-dimethyl-2-pyridinyl)methyl]sulfinyl}-1H-imidazo[4,5-b]pyridine; and
2-(3,4-dimethoxypyrid-2-yl)methanesulfinyl-5-difluoromethoxy-1H-benzimidazole.

EXAMPLE 3

2-{[3-Methyl-4-(3-methoxypropoxy)-2-pyridinyl) methyl]sulfinyl}-1H-benzimidazole (I)

Rabeprazole Sodium Salt

A 3-necked round-bottom flask equipped with reflux condenser, thermometer and magnetic stirring, under nitrogen atmosphere, is loaded with 2-[4-(3-methoxypropoxy)-3-methyl-1-oxypyridin-2-yl-methylsulfinyl]-1H-benzimidazole (intermediate II) (45.0 g; 111 mmols), methanol (270 ml), 30% sodium methoxide in methanol (20.1 g), tetramethylethylenediamine (77 g; 666 mmols) and $RuCl_3$ hydrate (40% w/w Ru; 1.2 g; 5.5 mmols). The reaction mixture is heated to 50° C. for 10 hours, then analyzed by HPLC (95% yield in solution). The mixture is cooled to room temperature, concentrated to half volume and diluted with 500 ml of water. The formed precipitate is filtered through Celite®. pH is adjusted to 6-7 first with acetic acid, then with sodium sulfite, and the mixture is extracted in ethyl acetate (300 ml). A sodium hydroxide 50% solution in water (440 mg; 111 mmols) is added to the mixture which is stirred for 24 hours at room temperature. The title product crystallized as polymorphic form β, disclosed in EP 1 674 463, in a purity higher than 99.7% (yield 91%).

EXAMPLE 4

2-{[3-Methyl-4-(3-methoxypropoxy)-2-pyridinyl)methyl]sulfinyl}-1H-benzimidazole (I)

Rabeprazole

A 3-necked round-bottom flask equipped with reflux condenser, thermometer and magnetic stirring, under nitrogen atmosphere, is loaded with 2-[4-(3-methoxypropoxy)-3-methyl-1-oxypyridin-2-yl-methylsulfinyl]-1H-benzimidazole sodium salt (intermediate II) (5.0 g; 13.0 mmols), dichloromethane (20 ml), triethylamine (16.5 g; 162 mmols). The reaction mixture is cooled to −10° C. and a solution of methylsulfonyl chloride (7.4 g; 65 mmols) in 10 ml of dichloromethane is dropped therein. After dilution with water, the phases are separated and the organic phase is evaporated to a residue. 2.3 g of product are obtained.

$^1$H NMR (DMSO-$d_6$): 1.96 (2H, m); 2.17 (3H, s); 3.22 (3H, s); 3.43 (2H, t); 4.08 (2H, t); 4.65 & 4.75 (2H, dd); 6.95 (1H, d); 7.25 (2H, m); 7.62 (2H, m); 8.21 (1H, d).

Following an analogous procedure, starting from the respective intermediate of formula (II), the following compounds are obtained:

2-(4-chloro-3-methoxypyrid-2-yl)methanesulfinyl-5-difluoromethoxy-1H-benzimidazole;

5-methoxy-2-{[(4-methoxy-3,5-dimethyl-2-pyridinyl)methyl]sulfinyl}-1H-benzimidazole;

5-methoxy-2-{[(4-methoxy-3-methyl-5-hydroxymethyl-2-pyridinyl)-methyl]sulfinyl}-1H-benzimidazole;

2-{[3-methyl-4-(2,2,2-trifluoroethoxy)-2-pyridinyl)methyl]sulfinyl}-1H-benzimidazole;

5-methoxy-2-{[(4-methoxy-3,5-dimethyl-2-pyridinyl)methyl]sulfinyl}-1H-imidazo[4,5-b]pyridine; and 2-(3,4-dimethoxypyrid-2-yl)methanesulfinyl-5-difluoromethoxy-1H-benzimidazole.

EXAMPLE 5

2-{[3-Methyl-4-(3-methoxypropoxy)-2-pyridinyl)methyl]sulfinyl}-1H-benzimidazole (I)

Rabeprazole

A 3-necked round-bottom flask equipped with reflux condenser, thermometer and magnetic stirring, under nitrogen atmosphere, is loaded with 2-[4-(3-methoxypropoxy)-3-methyl-1-oxypyridin-2-yl-methylsulfinyl]-1H-benzimidazole sodium salt (intermediate II) (7.5 g; 19.4 mmols), acetonitrile (30 ml), ethyldiisopropylamine (30.0 g; 232 mmols). The reaction mixture is cooled to −10° C. and methylsulfonyl chloride (7.8 g; 67.9 mmols) is dropped therein in 6 hours. Afterwards the reaction mixture is poured in 100 ml of water and added with NaOH to pH>13. The phases are separated, isopropyl acetate is added and the pH of the mixture is adjusted to about 9.5 with sodium hydrogen sulfite. The organic phase is separated and evaporated to a residue, which is taken up with acetonitrile. The product is crystallized. 4.8 g of the title product are obtained (Yield: 70%).

Following an analogous procedure, the following compounds are obtained:

2-(4-chloro-3-methoxypyrid-2-yl)methanesulfinyl-5-difluoromethoxy-1H-benzimidazole;

5-methoxy-2-{[(4-methoxy-3,5-dimethyl-2-pyridinyl)methyl]sulfinyl}-1H-benzimidazole;

5-methoxy-2-{[(4-methoxy-3-methyl-5-hydroxymethyl-2-pyridinyl)-methyl]sulfinyl}-1H-benzimidazole;

2-{[3-methyl-4-(2,2,2-trifluoroethoxy)-2-pyridinyl)methyl]sulfinyl}-1H-benzimidazole;

5-methoxy-2-{[(4-methoxy-3,5-dimethyl-2-pyridinyl)methyl]sulfinyl}-1H-imidazo[4,5-b]pyridine; and 2-(3,4-dimethoxypyrid-2-yl)methanesulfinyl-5-difluoromethoxy-1H-benzimidazole.

EXAMPLE 6

2-[4-(3-Methoxypropoxy)-3-methyl-1-oxypyridin-2-yl-methylsulfinyl]-1H-benzimidazole Intermediate II, Polymorphic Form I A 500 ml reactor equipped with water jacket, mechanical stirring, thermometer and under nitrogen, is loaded with 2-[4-(3-methoxypropoxy)-3-methyl-1-oxypyridin-2-yl-methylsulfinyl]-1H-benzimidazole potassium salt (20.0 g; 50.3 mmols), acetonitrile (200 ml) and water (40 ml). After dissolution of the substrate, the mixture is cooled to +20° C. and sodium hypochlorite (10.3% w/w; 40.8 g; 56.5 mmols) is dropped therein in 5 hours.

After that, sodium sulfite (5.0 g) is added, then sodium chloride until separation of the phases and pH is adjusted to =5 with formic acid. The aqueous phase is separated and re-extracted with ethyl acetate (2×50 ml), then the organic phases are combined and washed with a sodium chloride saturated solution. Upon concentration, the title product crystallizes. Yield: approximately 80%. The product has an XRPD spectrum as reported in FIG. 1 wherein the most intense diffraction peaks fall at 5.7; 11.6; 13.3; 18.2; 18.9; 20.6; 23.2; 23.6; 24.1; 24.8; ±0.2° in 2θ.

EXAMPLE 7

2-[4-(3-Methoxypropoxy)-3-methyl-1-oxypyridin-2-yl-methylsulfinyl]-1H-benzimidazole Intermediate II, Polymorphic Form II The product of example 6 can be further purified by suspension in methanol and addition of a stoichiometric amount of sodium methoxide to promote dissolution. The product is precipitated from the resulting solution by addition of a stoichiometric amount of acetic acid. The resulting precipitate is filtered, washed with methanol and dried in a static dryer. The recrystallization yield is 90%. The resulting product has an XRPD spectrum as reported in FIG. 2 wherein the most intense diffraction peaks fall at 5.5; 13.0; 18.4; 19.6; 20.3; 21.2; 22.4; 24.0; 25.1; 28.3 and 29.1±0.2° in 2θ.

The invention claimed is:

1. A process for the preparation of a compound of formula (I), or a salt thereof, either as a single isomer or as a mixture thereof,

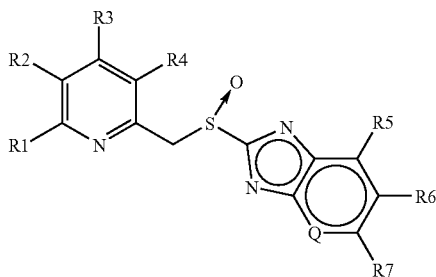
(I)

wherein

Q is $=CR_8-$ or $=N-$;

each of $R_1$, $R_2$, $R_3$ and $R_4$ is independently selected from hydrogen, halogen, hydroxy, nitro, $C_1-C_6$ alkyl optionally substituted by hydroxy; $C_1-C_6$ alkylthio; $C_1-C_6$ alkoxy optionally substituted by halogen or $C_1-C_6$ alkoxy; phenyl-$C_1-C_6$ alkyl; phenyl-$C_1-C_6$ alkoxy; and $-N(R_a R_b)$ wherein each of $R_a$ and $R_b$ is independently hydrogen or $C_1-C_6$ alkyl or $R_a$ and $R_b$, taken together with the nitrogen atom they are linked to, form a saturated heterocyclic ring; and each of $R_5$, $R_6$, $R_7$ and $R_8$ is independently selected from hydrogen, halogen, hydroxy; $C_1-C_6$ alkyl optionally substituted by hydroxy; $C_1-C_6$ alkylthio; $C_1-C_6$ alkoxy optionally substituted by halogen; $C_1-C_6$ alkyl-carbonyl, $C_1-C_6$ alkoxy-carbonyl, and oxazol-2-yl;

the process comprising the steps of:

(i) providing a compound of formula (II), or a salt thereof, either as an isomeric mixture, or as an individual isomer,

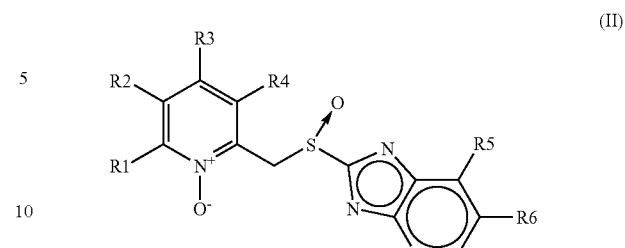
(II)

wherein Q and $R_1-R_7$ are as defined above; and (ii) performing a reduction reaction of the compound of formula (II), or the salt thereof, either as an isomeric mixture, or as an individual isomer, with a sulfonic acid chloride, in the presence of a basic agent.

2. The process according to claim 1, wherein a sulfonic acid chloride is selected from a $C_1-C_6$ alkylsulfonyl chloride, an aryl-$C_1-C_6$ alkylsulfonyl chloride, and an arylsulfonyl chloride.

3. The process according to claim 2, wherein a sulfonic acid chloride is a $C_1-C_4$ alkylsulfonyl chloride.

4. The process according to claim 1, wherein the basic agent is an alkali or alkaline-earth metal hydroxide or carbonate; a tertiary organic amine, a cyclic secondary amine, a cyclic tertiary amine, or a diamine.

5. The process according to claim 4, wherein the basic agent in the process of alternative a) is tetramethylethylenediamine or morpholine; and in the process of alternative b) is triethylamine or ethyldiisopropylamine.

6. The process according to claim 1, wherein the sulfonic acid chloride is a reducing agent and the stoichiometric ratio of the compound (II), or the salt thereof, to the reducing agent approximately ranges from 1.0 to 6.0.

7. The process according to claim 1, wherein the reduction reaction is performed in an organic aprotic solvent.

* * * * *